United States Patent [19]

Van Wijnsberghe et al.

[11] 4,021,445

[45] May 3, 1977

[54] PREPARATION OF 4-MONHOHALO-2-PYRAZOLIN-5-ON-COMPOUNDS

[75] Inventors: Leo August Van Wijnsberghe, 's-Gravenwezel; Raphaël Karel Van Poucke, Berchem, both of Belgium

[73] Assignee: AGFA-GEVAERT N.V., Mortsel, Belgium

[22] Filed: Nov. 25, 1975

[21] Appl. No.: 635,062

[30] Foreign Application Priority Data

Dec. 11, 1974 United Kingdom ............. 53616/74

[52] U.S. Cl. .......................................... 260/310 A
[51] Int. Cl.$^2$ ...................................... C07D 231/16
[58] Field of Search ............................... 260/310 A

[56] References Cited

UNITED STATES PATENTS 3,843,679  10/1974  Hoffman ....................... 260/310 A

OTHER PUBLICATIONS

Acta Chem. Scand. vol. 6, pp. 1499, 1512, 1513–1515 (1952).

*Primary Examiner*—Donald B. Moyer
*Attorney, Agent, or Firm*—A. W. Breiner

[57] ABSTRACT

A method is described for preparing 4-monohalo-2-pyrazolin-5-ones wherein a tertiary organic phosphite is allowed to react with a 4,4-dihalo-2-pyrazolin-5-one and the 4-monohalopyrazole-5-enol phosphate ester formed is hydrolyzed.

7 Claims, No Drawings

PREPARATION OF 4-MONHOHALO-2-PYRAZOLIN-5-ON-COMPOUNDS

The present invention relates to a new method for the preparation of 4-monohalo-2-pyrazolin-5-ones.

The formation of coloured photographic images by the coupling of oxidized aromatic primary amino developing agents with colour couplers is well known.

In subtractive three-colour photography it is common practice to form cyan, magenta and yellow dye images, the colours that are complementary to the primary colours. For the formation of the magenta separation image, usualy 2-pyrazolin-5-on couplers are used. These include 4-equivalent couplers, which are unsubstituted at the active methylene group in the 4-position and require four molecules of exposed silver halide to form one molecule of dyestuff as well as 2-equivalent couplers, wherein the active methylene group carries a substituent that is split off upon colour development, which require only two molecules of exposed silver halide for the formation of one molecule of dyestuff. One such substituent that is split off upon colour development is a halogen atom more particularly chlorine.

In U.S. Pat. No. 3,006,759 4-halo-2-pyrazolin-5-one couplers are prepared by halogenating the appropriate parent 2-pyrazolin-5-one coupler. Direct halogenation of 2-pyrazolin-5-ones, however, often leads to the formation of 4,4-dihalo-2-pyrazolin-5-ones or to mixtures of 4,4-dihalo- and 4-monohalo-2-pyrazolin-5-ones, especially when the pyrazolinone carries in the 3-position an amino or substituted amino group e.g. anilino, acylamino or ureido group.

In U.S. Pat. No. 3,522,051 2-pyrazolin-5-ones carrying in the 3-position an amino group or substituted amino group are chlorinated to form the corresponding 4-monochloro-2-pyrazolin-5-one by chlorination with chlorine or sulphuryl chloride in the presence of a Friedel Crafts metal halide catalyst more particularly aluminium chloride. Though the method described in the latter U.S. Patent is satisfactory for many compounds it also occurs that dihalogenated byproducts are formed especially when the 3-position carries an anilino group.

In accordance with the present invention a simple method is provided for the preparation of pure 4-monohalo-2-pyrazolin-5-one compounds in general and particularly for those comprising in the 3-position an amino group or substituted amino group, more particularly an acylamino or anilino group.

It has been found that 4-monohalo-2-pyrazolin-5-ones can be prepared quantitatively from the corresponding 4,4-dihalo-2-pyrazolin-5-ones which, as is known, can be prepared quantitatively with a high degree of purity by simple halogenation.

According to the method of the present invention, 4-manohalo-2-pyrazolin-5-ones are prepared by reaction of a 4,4-dihalo-2-pyrazolin-5-one with a tertiary organic phosphite especially a trialkyl or triaryl phosphite e.g. triethyl phosphite and subsequent hydrolysis of the 4-mono-halopyrazole-5-enol phosphate ester formed.

The method of the present invention can be represented by means of the following reaction scheme

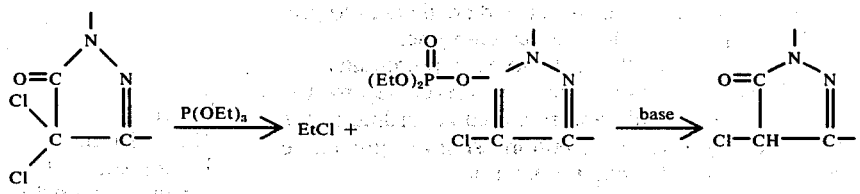

The method of the present invention can be generally applied for the formation of the 4-monohalo derivatives of the known 2-pyrazolin-5-one colour couplers and intermediate 2-pyrazolin-5-ones therefor e.g. 3-amino-2-pyrazolin-5one. Thus, the 2-pyrazolin-5-ones that can be prepared according to the method of the present invention can be represented by the general formula:

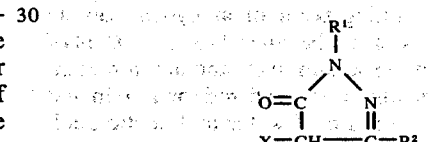

wherein

X stands for halogen e.g. bromine or chlorine, and each of $R^1$ and $R^2$ are substituents of the type well-known in 2-pyrazolin-5-one colour couplers or intermediates therefor.

The 4-monohalo-2-pyrazolin-5-ones are obtained with a high degree of purity and generally need not be recrystallized.

In the above general formulae $R^1$ and $R^2$ are substituents of the type commonly present in 2-pyrazolin-5-one colour couplers. $R^1$ can be e.g. alkyl of 1 to 20 C-atoms including substituted alkyl e.g. haloalkyl e.g. trifluoroethyl, cyanoalkyl and benzyl including substituted benzyl, aryl including substituted aryl e.g. phenyl and phenyl substituted by one or more of halogen e.g. chlorine, alkyl, alkoxy, aroxy e.g. phenoxy, alkylthio, alkylsulphonyl, alkylsulphamoyl, haloalkoxy, haloalkylthio, haloalkysulphenyl, etc., or a 5- or 6-membered heterocycle including a substituted heterocycle. $R^2$ can be e.g. an alkyl group or alkoxy group of 1 to 20 C-atoms, an amino group including a substituted amino group e.g. anilino including substituted anilino e.g. aninilo substituted with one or more of halogen e.g. chlorine, suplho, nitro, cyano, alkoxy, alkylsulphonyl, alkylthio, acylamino, N-alkylsulphamoyl, etc., acylamino e.g. alkyl- and aryl-carbonamido or -ureido wherein the alkyl and aryl group may carry substituents e.g. alkyl, alkoxy, alkylthio, alkylsulphonyl, phenoxy, acylamino, etc.

The method of the invention is of particular importance for the preparation of 4-monohalo-2-pyrazolin-5-ones carrying in the three position an acylamino or an anilino group.

The method according to the present invention generally occurs by reaction of triethylphosphite with the 4,4-dihalo-2-pyrazolin-5-one in an inert organic solvent e.g. benzene or acetonitrile at normal atmospheric pressure and a temperature comprised between about 10° C and about 80° C, preferably betwwen about 20° C and 50° C whereupon the solvent is removed and base is added.

The phosphite is usually employed in a molar amount slightly exceeding that of the 4,4-dihalo-2-pyrazolin-5-one. After hydrolysis, the reaction mixture can be poured into a mixture of water and acetic acid to precipitate the 4-monohalo-2-pyrazolin-5-one.

The table hereinafter lists some representative 4-mono-halo-2-pyrazolin-5-ones corresponding to the above general formula and prepared according to the method of the present invention using the procedure set forth in the following preparation.

PREPARATION 0.1 mole (35.46 g) of 1-phenyl-3-(4-chloroanilino)-4,4-dichloro-2-pyrazolin-5-one, prepared by dichlorination of colour coupler n°4 of British Pat. NO. 1,069,534, was dissolved in 200 ml of benzene whereupon 0.11 mole (19.6 ml) of triethyl phosphite dissolved in 50 ml of benzene was added. The mixture was stirred for 30 min at 30° C and the benzene was then removed by evaporation. To the 1-phenyl-3-(4-chloroanilino)-4-chloro-5-diethoxy phosphate-pyrazole formed (melting point of analytical sample recrystallized from benzene/hexane : 113° C) 100 ml of a solution of 0.02 mole sodium methanolate in methanol were added. The mixture was stirred for 15 min and then poured into a mixture of water and acetic acid. The precipitate of compound 3 in the table hereinafter was filtered by suction and dried. Melting point : 210° C.

intermediates for the preparation of other 2-equivalent couplers including so-called DIR- and BIR-couplers, i.e. Development Inhibitor Releasing couplers and Bleach Inhibitor Releasing couplers.

We claim:

1. Method for the preparation of a 4-monohalo-2-pyrazolin-5-one having the formula:

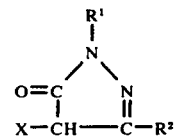

wherein:

X is halogen, $R^1$ represents $C_1$-$C_{20}$ alkyl, haloalkyl, cyanoalkyl, benzyl, phenyl or phenyl substituted with one or more members selected from the group consisting of halogen, alkyl, alkoxy, aroxy, alkylthio, alkylsulphonyl, alkylsulphamoyl, haloalkoxy, haloalkylthio and haloalkylsulphonyl, represents (1) anilino or anilino substituted with one or more members selected from the group consisting of halogen, sulpho, nitro, cyano, alkoxy, alkylsulphonyl, alkylthio, acylamino and N-alkylsulphamoyl, and (2) alkyl- or aryl-carbonamido or -ureido wherein the alkyl or aryl groups may carry one or more members selected from the group consisting of alkyl, alkoxy, alkylthio, alkylsulphonyl, phenoxy and acylamino, comprising the steps of reaction of a trialkylphosphite with a 4,4-dihalo-2-pyrazolin-5-one carrying in the 1- and 3-positions substituents $R^1$ and $R^2$ as defined, and subsequent hydrolysis of the 4-monohalopyrazole-5-enol phosphate ester formed.

2. Method according to claim 1, wherein reaction of

Table

| Compound | R₁ | R₂ | X |
|---|---|---|---|
| 1 | phenyl | amino | Cl |
| 2 | do | methyl | Cl |
| 3 | do | 4-chloro-anilino | Cl |
| 4 | 2,4,6-trichlorophenyl | 4-nitroanilino | Cl |
| 5 | do | 4-methylsulphonylanilino | Cl |
| 6 | do | 4-n-hexadecylsulphonylanilino | Cl |
| 7 | do | 4-[β-(3'-n-pentadecyl-phenoxy)ethoxycarbonylamino]anilino | Cl |
| 8 | do | 2-chloro-5-N-methyl-N-n-hexadecylsulphamoylanilino | Cl |
| 9 | do | 2-chloro-5-myristamido-anilino | Cl |
| 10 | do | 3-(2',4'-ditert.amyl-phenoxy-acetamido)benzamido | Cl |
| 11 | 2,2,2-trifluoroethyl | 4-N-methyl-N-n-hexadecyl-sulphamoyl anilino | Cl |
| 12 | α-trifluoromethyl-benzyl | 2-chloro-5-(2'-cyclopentyl-4'-tert.butyl-phenoxy sulphonyl)anilino | Cl |
| 13(a) | 2-chloro-4-N-methyl-N-n-hexadecylsul-phamoylphenyl | 4-N,N-dimethylsulphamoyl-anilino | Cl |
| 14(b) | 3,4-dichlorophenyl | 2-chloro-5-N-methyl-N-n-hexadecyl-sulphamoyl anilino | Cl |

(a)1-(2'-chloro-4'-N-methyl-N-n-hexadecylsulphamoylphenyl)-3-(4'-N,N-dimethylsulphamoyl anilino)-2-pyrazolin-5-one and
(b)1-(3',4'-dichlorophenyl)-3-(2'-chloro-5'-N-methyl-N-n-hexadecylsulphamoylanilino)-2-pyrazolin-5-one were prepared as described in French Patent 2,106,154.

The 4-monohalo-2-pyrazolin-5-one compounds prepared according to the method of the present invention can be used as 2-equivalent colour couplers in silver halide colour photography. They can also be used as the tertiary phosphite with the 4,4-dihalo-2-pyrazolin-5-one occurs in an inert organic solvent.

3. Method according to claim 2, wherein the said organic solvent is benzene or acetonitrile.

4. Method according to claim 1, wherein the said reaction occurs at a temperature between about 10° and about 80° C.

5. Method according to claim 1, wherein the trialkyl phosphite is triethyl phosphite.

6. Method according to claim 1, wherein $R^2$ is an acylamino group.

7. Method according to claim 1, wherein $R^2$ is an anilino group.

* * * * *

UNITED STATES PATENT AND TRADEMARK OFFICE
CERTIFICATE OF CORRECTION

PATENT NO. : 4,021,445
DATED : May 3, 1977
INVENTOR(S) : Leo August VAN WIJNSBERGHE ET AL It is certified that error appears in the above-identified patent and that said Letters Patent are hereby corrected as shown below:

Heading, in the title at [54], "4-MONHOHALO-2" should read
-- 4-MONOHALO-2 --;

Column 1, in the title, "4-MONHOHALO-2" should read
-- 4-MONOHALO-2 --;

Column 1, line 26, "5-on" should read -- 5-one --;

Column 2, line 2, "4-manohalo - 2-" should read -- 4-monohalo-2-  --;

Column 4, claim 1, line 23, "represents" should read -- $R^2$ represents --

Signed and Sealed this

*Fifteenth* Day of *November 1977*

[SEAL]

Attest:

RUTH C. MASON
*Attesting Officer*

LUTRELLE F. PARKER
*Acting Commissioner of Patents and Trademarks*